United States Patent
Geslot

(10) Patent No.: US 10,328,167 B2
(45) Date of Patent: Jun. 25, 2019

(54) INSTALLATION FOR STERILIZATION ARTICLES BY RADIATION

(71) Applicant: Serac Group, La Ferte Bernard (FR)

(72) Inventor: Nicolas Geslot, Lamnay (FR)

(73) Assignee: SERAC GROUP, La Ferte Bernard (FR)

( * ) Notice: Subject to any disclaimer, the term of this patent is extended or adjusted under 35 U.S.C. 154(b) by 0 days.

(21) Appl. No.: 15/181,875

(22) Filed: Jun. 14, 2016

(65) Prior Publication Data

US 2016/0361451 A1 Dec. 15, 2016

(30) Foreign Application Priority Data

Jun. 15, 2015 (FR) .................... 15 55447

(51) Int. Cl.
| | |
|---|---|
| *A61L 2/08* | (2006.01) |
| *B65B 55/04* | (2006.01) |
| *A61L 2/26* | (2006.01) |
| *B65B 55/08* | (2006.01) |
| *B67B 3/00* | (2006.01) |

(52) U.S. Cl.
CPC ............. *A61L 2/087* (2013.01); *A61L 2/26* (2013.01); *B65B 55/08* (2013.01); *B67B 3/003* (2013.01); *A61L 2202/23* (2013.01)

(58) Field of Classification Search
None
See application file for complete search history.

(56) References Cited

U.S. PATENT DOCUMENTS

| | | | |
|---|---|---|---|
| 2005/0158218 A1* | 7/2005 | Dumargue | A23L 3/26 422/121 |
| 2009/0013645 A1* | 1/2009 | Mastio | A61L 2/082 53/425 |
| 2011/0084221 A1* | 4/2011 | Eguchi | A23L 3/26 250/492.3 |
| 2011/0142731 A1 | 6/2011 | Beckmann et al. | |
| 2012/0134878 A1* | 5/2012 | Silvestri | A61L 2/087 422/22 |
| 2013/0140470 A1* | 6/2013 | Fallet | A61L 2/087 250/453.11 |
| 2013/0161532 A1* | 6/2013 | Naka | A61L 2/087 250/455.11 |
| 2013/0193344 A1* | 8/2013 | Drenguis | A61L 2/10 250/455.11 |
| 2013/0272920 A1* | 10/2013 | Knott | A61L 2/087 422/22 |

(Continued)

FOREIGN PATENT DOCUMENTS

| | | | | |
|---|---|---|---|---|
| EP | 1 749 747 A1 | 2/2007 | | |
| EP | 1749747 A1 * | 2/2007 | ........... | B65B 7/2807 |

(Continued)

*Primary Examiner* — Michael J Logie
(74) *Attorney, Agent, or Firm* — Muncy, Geissler, Olds & Lowe, P.C.

(57) ABSTRACT

An installation for sterilizing articles by radiation, the installation having a radiation-generator device and an article support device disposed facing the radiation-generator device. Devices for moving the articles in front of the radiation-generator device are provided. The article support device comprises devices for varying the orientation of the articles when the articles move in front of the radiation-generator device.

9 Claims, 2 Drawing Sheets

(56) References Cited

U.S. PATENT DOCUMENTS

2014/0124681 A1* 5/2014 Trevisan ................. B67B 3/003
250/455.11

FOREIGN PATENT DOCUMENTS

| EP | 2 149 500 A1 | 2/2010 | | |
|----|--------------|--------|---|---|
| FR | 2 865 135 A1 | 7/2005 | | |
| JP | 11-193009 A | 7/1999 | | |
| JP | 2011251708 A | * 12/2011 | ............. | B67B 3/003 |

* cited by examiner

INSTALLATION FOR STERILIZATION ARTICLES BY RADIATION

The present invention relates to an installation for sterilizing articles, in particular bottle caps or bottles, by radiation.

BACKGROUND OF THE INVENTION

It is known that when sterilizing articles by radiation, in particular with electron bombardment, it is desirable for the radiation to reach the surfaces that are to be treated directly because of the attenuation caused by any obstacle in the path of the radiation.

To this end, an installation for sterilizing articles is known from document FR-A-2 865 135, which installation comprises two electron bombardment members disposed at different orientations relative to the articles that are to be sterilized. Thus, by appropriately positioning the electron bombardment members as a function of the shape of the articles to be sterilized, it is possible to ensure that each electron bombardment member is facing a small-thickness portion of the article, in such a manner that it is possible to sterilize each portion of the article with electron bombardment at low energy.

That installation presents the drawback of requiring at least two radiation-generator devices, which are burdensome both because of their cost and because of the steps that must be taken in order to avoid radiation leaking, which is dangerous for the health of operators of the installation.

OBJECT OF THE INVENTION

The invention aims to provide an installation for sterilizing articles while minimizing the number of radiation-generator devices required for satisfactory sterilization of the articles.

BRIEF SUMMARY OF THE INVENTION

With a view to fulfilling this aim, the invention provides an installation for sterilizing articles by radiation, the installation comprising: a radiation-generator device and an article support device disposed facing the radiation-generator device and including means for moving the articles in front of the radiation-generator device; and means for varying the orientation of the articles while the articles are moving in front of the radiation-generator device.

Thus, portions of the articles that were not subjected to the radiation in a first orientation, are subjected to radiation during variations in the orientation of the articles, so that it is possible to increase the surface area treated with a single generator.

In an advantageous version of the invention, the article support device comprises means for moving articles in a first direction, and means for varying the orientation of the articles in a second direction, different to the first direction. Preferably, the means for varying the orientation of the articles in a second direction comprise means for putting the articles into rotation about an axis of rotation that forms an angle, preferably a right angle, with the first direction.

In another advantageous aspect of the invention, the article support device includes an article movement member, configured to move the articles along a circular path about a first axis of rotation and means for rotating the articles about a second axis of rotation extending radially relative to the circular path.

In a first embodiment for use with the cylindrical articles of circular section, the installation comprises a stationary work surface having an annular track and a rotary platform that is mounted to turn about an axial direction of the annular track and that includes recesses overlying the annular track, the recesses being dimensioned so that an article engaged in a recess rests on the annular track.

In a second embodiment, for use with the cylindrical articles of circular section, the installation comprises a stationary work surface including an annular track and a rotary platform that is mounted to turn about an axial direction of the annular track and that includes an annular portion overlying the annular track and in contact with the cylindrical articles in order to cause them to turn about a radial direction of the annular track.

Preferably, the installation comprises first and second rotary platforms and transfer means for transferring the articles from the first platform to the second platform, the transfer means being arranged to swap over the faces of each article that are subjected to radiation.

In yet another embodiment, more particularly adapted to sterilizing bottles, the article support device includes an article movement member configured to move articles along a circular path about a first axis of rotation, and means for rotating articles about a second axis of rotation extending parallel to the first axis of rotation.

BRIEF DESCRIPTION OF THE DRAWINGS

Other characteristics and advantages of the invention also appear on reading the following description of a non-limiting, preferred embodiment of the invention with reference to the accompanying figures, in which.

DETAILED DESCRIPTION OF THE INVENTION

Figure 1:
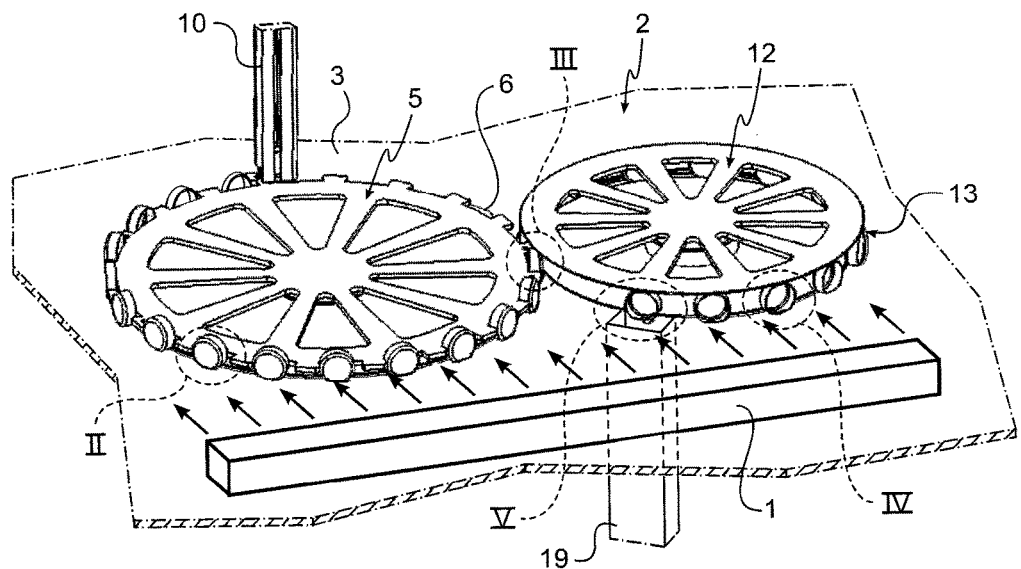
FIG. 1 is a diagrammatic perspective view of the invention.
Figure 2:
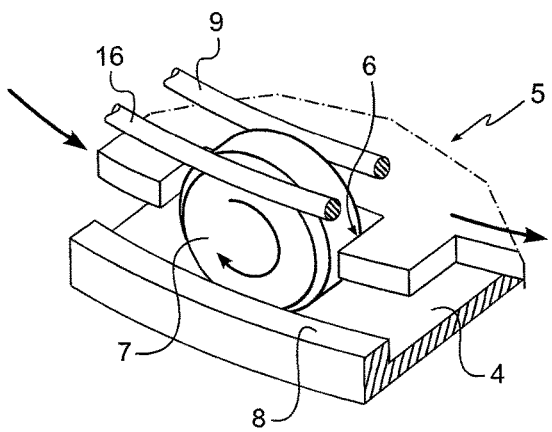
FIG. 2 is a larger-scale and more detailed view of a detail II of FIG. 1.
Figure 3:
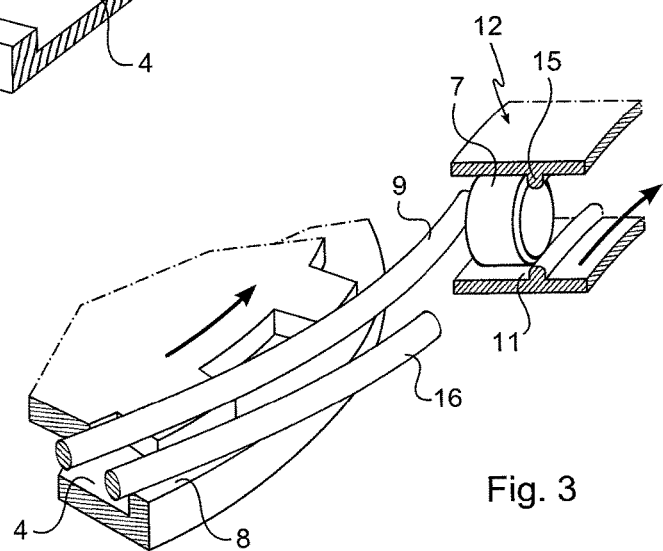
FIG. 3 is a larger-scale and more detailed view of a detail III of FIG. 1.
Figure 4:
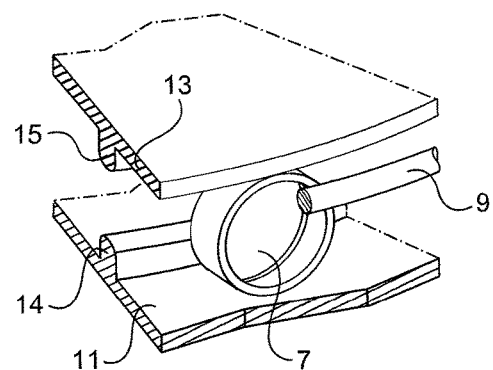
FIG. 4 is a larger-scale and more detailed view of the detail IV of FIG. 1.
Figure 5:
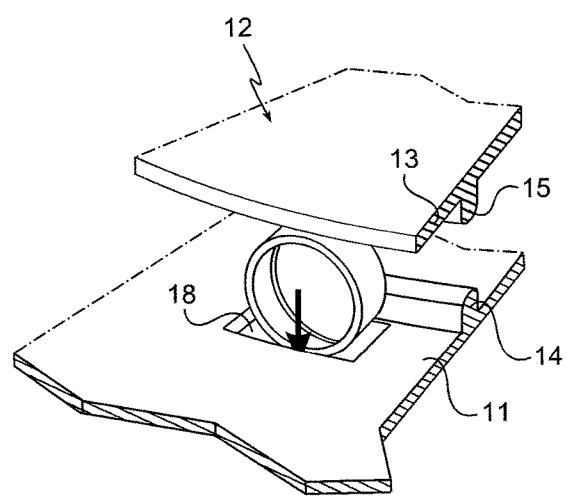
FIG. 5 is a larger-scale and more detailed view of the detail V of FIG. 1.

With reference to FIGS. 1 to 5, the installation shown is designed for sterilizing bottle caps. To this end, the installation comprises a radiation-generator device 1, and an article support device 2 disposed facing the radiation-generator device.

The article support device 2 comprises a stationary work surface 3 including a first annular track 4, and also a first rotary platform 5 that is mounted to turn about an axial direction of the annular track 4. The rotary platform 5 includes recesses 6 overlying the annular track 4. The recesses 6 are dimensioned so that a cap engaged in a recess rests via its edge face on the annular track 4. Furthermore, the platform 5 is spaced apart from the track 4 so that the rear edge of a recess, relative to the direction of rotation of the platform, comes to bear against a cap substantially half way up it, i.e. at its horizontal diameter. On the outer side of the track 4, relative to the axis of rotation, the recesses 6 are open and the caps 7 are held in the recesses by a lip 8 projecting from the outer edge of the annular track. In their top portions, the caps are held by inner and outer guide rails 9 and 16. Thus, during rotation of the platform 5, the caps 7 are driven in rotation about a direction that is radial relative to the annular track 4.

Access to the recesses from the top is totally free so that in order to feed caps to the platform 5 it suffices to provide a column 10 in which the caps are stacked on their edge faces, and to mount the column 10 on the work surface in such a manner that it overlies the recesses 6. In the embodiment shown, the caps 7 are engaged in the recesses 6 with their tops facing outwards.

The installation further comprises a second annular track 11 with which a second rotary platform 12 is associated.

As mentioned above, the rotary platform 12 is mounted to turn about an axial direction of the annular track 11. In this embodiment, the platform 12 comprises an annular portion 13 overlying the annular track 11 and that is in contact with the caps 7 in order to cause them to turn about a radial direction of the annular track 11. On the inner side, relative to a radial direction of the annular track 11, the caps are held by a lip 14 projecting relative to the annular track 11, and by a lip 15 projecting downwards relative to the annular portion 13 of the platform 12. On the outer side, the caps are held by a slide 9 supported by the work surface by means of arms (not shown).

The two platforms 5 and 12 turn in opposite directions in order to make transfer possible via the guide rails 9 and 16. In the transfer zone, the lip 8 is interrupted. In the embodiment shown, the outer guide rail 16 is also interrupted after the transfer zone, but it could be configured to extend perpendicularly to the track 11 and to provide internal guidance for the caps. It should be observed that because of the opposite directions of rotation of the platforms and because transfer is direct from the first platform to the second platform, the faces of each cap that are subjected to radiation is swapped over during transfer. This makes it possible to treat both faces of the cap with a single radiation-generator device. At the end of the travel of the caps 7, they fall through an opening 18 in the annular track 11 and are recovered by a transfer chute 19 that takes them to the zone of use.

Figure 6:
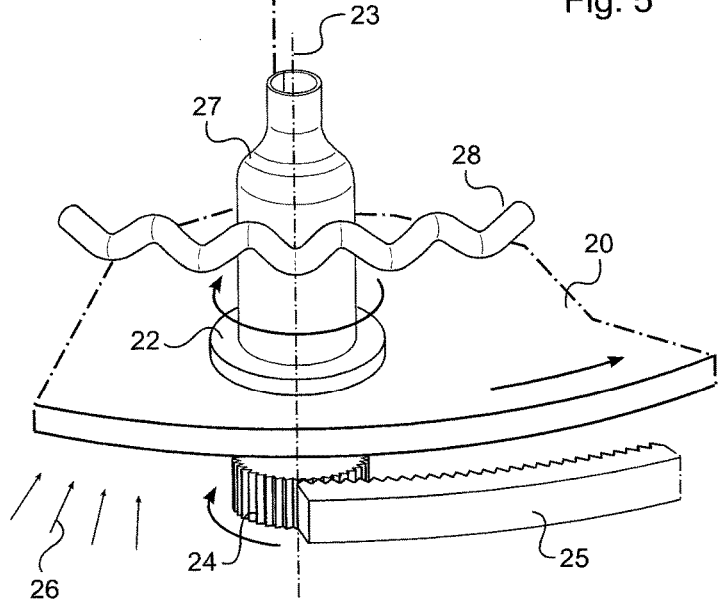
FIG. 6 is a fragmentary diagrammatic perspective view of an embodiment of the invention suitable for sterilizing bottles.

With reference to FIG. 6, the installation includes a rotary platform 20 mounted to turn about an axis of rotation 21 on a work surface (not shown). Plates of which only one is shown in the figure, are carried by the platform, each of which is mounted to turn about a respective axis of rotation 23 that is parallel to the axis of rotation 21. Each plate 22 is associated with a pinion 24 that meshes with a toothed sector 25 carried by the work surface in the radiation zone represented by the arrows 26. A bottle 27 is placed on each plate, with its axis of symmetry coinciding with the axis of rotation 23. A guide 28 connected to the frame holds the bottle laterally. In order to avoid the guide 28 obstructing radiation, the guide 28 has a zigzag structure in a vertical plane.

Naturally, the invention is not limited to the embodiment described and variants may be applied thereto without going beyond the ambit of the invention, as defined by the claims.

In particular, although the invention is described for sterilizing caps or bottles, it may also be used for other cylindrical articles of circular section, or even for non-cylindrical articles.

Although in the embodiment shown the articles are carried by rotary platforms turning in opposite directions, the invention may be performed with rotary platforms turning in the same direction, the transfer means being adapted accordingly to swap over the faces of the articles that are subjected to radiation.

Although the invention is described with a single electron bombardment device, it is possible that for some articles it is necessary to provide a plurality of electron bombardment devices. In no way does that detract from the advantages of the invention, which makes it possible to increase the surface area treated by each of the electron bombardment devices.

The invention claimed is:

1. An installation for sterilizing by radiation articles having a cylindrical surface of circular section and a closed end having an internal face and an external face, the installation comprising a radiation-generator device and an article support device disposed facing the radiation-generator device, the radiation-generator device including an electron bombardment member, the article support device comprising a stationary work surface including a first annular track and a second annular track on which the cylindrical surface of the articles rests, each of the annular tracks having a portion adjacent to said radiation-generator device, a first rotary platform and a second rotary platform being mounted to turn around an axial direction of the first annular track and the second annular track respectively for moving the articles in front of the radiation-generator device by making the articles rotating around a central axis of the article and rolling in front of the radiation-generator device, said central axis of the article being aligned with a radius of each platform and parallel to said radius of each platform, the installation comprising transfer means for transferring the articles from the first platform to the second platform, the transfer means being arranged to swap over the faces of each article that are subjected to radiation.

2. The installation according to claim 1, wherein the first rotary platform includes recesses overlying the annular track, the recesses being dimensioned so that an article engaged in a recess rests via its cylindrical surface on the annular track.

3. The installation according to claim 2, wherein the platform is spaced apart from the track so that recesses have a rear edge, relative to the direction of rotation of the platform, coming to bear against the cap substantially half way up it.

4. The installation according to claim 2, wherein the device is arranged so that access to the recesses is obtained from a top of the device without obstruction.

5. The installation according to claim 1, wherein the second rotary platform includes an annular portion overlying the annular track and that is in contact with the cylindrical surface of the articles.

6. The installation of claim 1, wherein the platforms rotate in opposite directions.

7. The installation of claim 1, wherein a portion of the second platform extends above a portion of the first platform in a transfer zone for directly transferring the articles from one of the platforms to the other.

8. The installation of claim 1, wherein the radiation-generator device extends along one side of the installation.

9. The installation of claim 8, wherein the radiation-generator device comprises only one electron-bombardment member extends along said side of the installation.

* * * * *